United States Patent
Heege et al.

(10) Patent No.: US 10,517,772 B2
(45) Date of Patent: Dec. 31, 2019

(54) NONWOVEN UNIT (71) Applicant: ONTEX BVBA, Buggenhout (BE)

(72) Inventors: Thomas Heege, Duengenheim (DE); Rudolf Heege, Kaisersesch (DE)

(73) Assignee: Ontex BVBA, Buggenhout (BE)

( * ) Notice: Subject to any disclaimer, the term of this patent is extended or adjusted under 35 U.S.C. 154(b) by 0 days.

(21) Appl. No.: 16/065,674

(22) PCT Filed: Dec. 23, 2016

(86) PCT No.: PCT/EP2016/082546
§ 371 (c)(1),
(2) Date: Jun. 22, 2018

(87) PCT Pub. No.: WO2017/109166
PCT Pub. Date: Jun. 29, 2017

(65) Prior Publication Data
US 2019/0008697 A1 Jan. 10, 2019

(30) Foreign Application Priority Data

Dec. 23, 2015 (EP) ................................. 15202486

(51) Int. Cl.
*B32B 38/00* (2006.01)
*A61F 13/20* (2006.01)
*B32B 37/22* (2006.01)

(52) U.S. Cl.
CPC .......... *A61F 13/2094* (2013.01); *B32B 37/22* (2013.01); *B32B 38/0004* (2013.01); *B32B 2555/02* (2013.01)

(58) Field of Classification Search
CPC .............. A61F 13/2094; A61F 13/2082; A61F 13/15699; B32B 27/22; B32B 38/0004
See application file for complete search history.

(56) References Cited

U.S. PATENT DOCUMENTS

| 4,816,100 A * | 3/1989 | Friese ................... A61F 13/206 156/191 |
| 5,235,515 A * | 8/1993 | Ungpiyakul ...... A61F 13/15699 700/125 |
| 2003/0075278 A1 | 4/2003 | Schoelling |

(Continued)

FOREIGN PATENT DOCUMENTS

| DE | 3519515 A1 | 12/1986 |
| EP | 1132325 A2 | 9/2001 |

(Continued)

OTHER PUBLICATIONS

PCT Search Report and Written Opinion for PCT/EP2016/082546, dated Feb. 13, 2017.

(Continued)

*Primary Examiner* — Mark A Osele
*Assistant Examiner* — Christopher C Caillouet
(74) *Attorney, Agent, or Firm* — Vivicar Law, PLLC (57) ABSTRACT

The current invention concerns an improved method for intermittently providing strips of a continuous first web material onto a continuous second web material, in particular a method for manufacturing tampon blanks, in a continuous process, thus avoiding the disadvantages of stop-and-go methods. Furthermore, an apparatus or system is provided for executing said methods.

10 Claims, 3 Drawing Sheets

(56) References Cited

U.S. PATENT DOCUMENTS

2009/0288765 A1* 11/2009 Showole ................ A61F 13/58
                                                                156/250
2010/0130907 A1*  5/2010 Linkel ................... A61F 13/206
                                                                 604/11
2014/0115847 A1    5/2014 Tomsovic et al.

FOREIGN PATENT DOCUMENTS

| EP | 1308147 A2 | 5/2003 |
| EP | 2260813 A1 | 12/2010 |
| WO | 1999027878 A1 | 6/1999 |
| WO | 0101908 A1 | 1/2001 |

OTHER PUBLICATIONS

Office Action in European Application No. 15202486.5, dated Apr. 13, 2017.

* cited by examiner

NONWOVEN UNIT

CROSS-REFERENCE TO RELATED APPLICATIONS

This application is the national stage application of corresponding international application number PCT/EP2016/082546, filed Dec. 23, 2016, which claims priority to and the benefit of European application no. 15202486.5, filed Dec. 23, 2015, all of which are hereby incorporated by reference in their entirety.

TECHNICAL FIELD

The invention pertains to the technical field of manufacturing (digital) tampon blanks, tampons, and intermediate products thereof. More in particular, the invention describes an improved method for intermittently providing strips onto a continuous web material in a continuous fashion. Furthermore, the invention relates to an improved method for producing tampon blanks, and an apparatus for doing so, as well as the product manufactured by said method.

BACKGROUND

Tampons are well known in the art and are used for feminine hygiene. Also many tampon manufacturing methods and apparatuses have been disclosed in the prior art. Generally, a distinction is made between folded and rolled tampons. The former have improved absorbent characteristics, but possess less strength and are commonly used with an applicator to reduce the chance of tears and other damage to the tampon before insertion. Rolled tampons are slightly less absorbent, but more sturdy and can be applied digitally, as opposed to the folded tampons. Furthermore, measures can be taken to increase the absorbency of the rolled tampons. The invention will focus on uses concerning rolled tampons and intermediate products thereof.

Rolled tampons are manufactured by rolling multiple-layered sheets. The multiple-layered sheets comprise a layer of absorbent material of a certain length, upon which a strip of web material is bonded which has only a fraction of the length of the layer of the absorbent material, thus creating the multiple-layered sheets. An example of this can be seen in FIG. 1A. A further description of this product will be provided later in this document.

It is precisely the difference in length between the absorbent material and the strip of web material that causes problems in the production process and the apparatuses used therefor. Most of these operate under stop-go circumstances, where the shorter strip is provided intermittently to a sealing or bonding station for bonding the strip to the longer absorbent material over parts of these materials. In order to intermittently provide the strips, a conveying system is used which operates under cyclic conditions, whereby a square wave is approximated with relatively short rise and fall time.

First of all, it is desired to attain a maximal production speed, therefore the industry strives for continuous processes, allowing the materials to be conveyed at constant (high) speeds. Intermittent processes would require an acceleration and deceleration each cycle, which would be restricted by mechanical limitations. A continuous process could run at higher speeds compared to a stop-go process, as it would not require such high accelerations and decelerations, as the frequency of these cycles can easily run up to several cycles per second. A high production speed of this part of the system is also necessary, as preceding processes and following processes, and the apparatuses used in them, have improved significantly, while the process of actually creating the multiple-layered sheets has somewhat lagged behind due to the restrictions set by using stop-go processes.

Another consequence of the high frequency of the acceleration and deceleration cycles, and the short rise and fall time of the cycles, is the strain this would impose on the apparatuses operating under such a stop-go process. These apparatuses would be far more prone to mechanical breakdowns, requiring costly repairs and spare parts. Furthermore, a system capable of performing high-frequency stop-go processes will generally be more expensive than a system that runs continuously at constant speeds. Also, apparatuses for stop-go processes will generally require more space than continuous apparatuses.

Thirdly, stop-go processes are much harder to regulate, especially when accurate coordination of the stop-go process with other processes is needed. Small variations easily occur due to the delicate course of the cycle, especially considering the very short period of the cycles, and furthermore due to the high frequency, variations are more likely to show up in some or more products. A continuous process is less sensitive to these variations, resulting in smaller variations if they occur. Furthermore, a continuous process can be more easily monitored and adjusted.

Such a stop-go process is for instance described in DE 3,519,515, where a first material is cut into short strips and affixed to a continuously provided second material. The first material is usually conveyed intermittently by a combination of multiple rollers to eventually be bonded to the second material. This has the aforementioned disadvantages the applicant wishes to avoid. In a second example according to the invention of DE 3,519,515, a fully continuous process is briefly discussed according to FIG. 3. In this single example however, it is not clear how the invention wishes to convey the first material at a first low speed before cutting it into strips, and at the same time, convey the second material at a second, higher, speed than the first speed, as the conveying of the second roller would be executed by the same roller which therefore would rotate at two different speeds if strips are to be provided of a different length than corresponding sections of the second material. As a result, the proposed concept of FIG. 3 would not be able to work and would therefore not enable a continuous process.

A well-known and widely-used prior art process and apparatus for manufacturing tampon blanks or intermediate products thereof has been developed by Ruggli. Herein two separate conveying systems are used, wherein the conveying systems use rollers to guide and pull two web materials, one of which is strongly absorbent. The first web material is divided into strips which are provided intermittently in a stop-go process to the second web material, which has been perforated along transverse lines. It is important to note that the length of the strips is shorter than the length of the segments of the second web material, demarcated by the perforation lines, this being the reason a stop-go process is used at a high frequency and high speeds. As mentioned, the applicant noticed that the use of the Ruggli apparatus and the associated method results in a high strain on the components of the stop-go system, which causes more mechanical breakdowns and significantly higher maintenance costs. Furthermore, the applicant notices that the production speed is capped at a lower rate than is desired, as the systems that follow or precede the Ruggli apparatus can operate at higher speeds and are thus forces to lower their speed to match the Ruggli apparatus.

In a first solution, according to EP 1,308,147, a continuous process is proposed wherein strips are cut and then reoriented (preferably a quarter turn) which comes down to the practical switching of the length and breadth of the strips. This enables the user to run the system for producing strips at an equal speed to a second system that provides a second material to which the strips are bonded in such a way that the length of a strip differs from the length of the second material to which the strip is associated. The disadvantage of this system is that reorienting the strip is a complicated process with a relatively high margin of error, and needs expensive machinery. Furthermore, it requires more space than other systems as the reorienting needs to happen between the cutting of the strips, and the joining of the strips to the second material. In practical applications, these processes are preferably executed as close to each other as possible, both in time as in space.

In a second solution, according to EP 2,260,813, a device is proposed which is capable of gripping the strips and stretching these before applying the strips to a second material. Again, this requires sophisticated, expensive machinery and space, and adds more breakdown points to the process. Furthermore, it offers no real solution as the stretched material will try to revert to its previous state and thus deform the product.

In a third solution, according to EP 1,035,819, a first material is provided continuously to a suction roller at a first speed where the first material is accelerated to a second speed and stretched, and subsequently cut into shorter strips. The strips are conveyed to a second web material, continuously provided at a second speed higher than the first speed, where the strips are bonded to the second web material. Disadvantages of the proposed concept are, as can be seen in the figures, the need for an elaborate system of pre-cutting rollers (for weakening the separation zones of the strips), acceleration rollers (for accelerating and tearing off the separate strips), transfer drums, and a suction drum which is difficult to accurately control. Larger systems are usually more prone to technical failures, due to the multitude of components which affect each other. Furthermore, the longer the path the strips and other items must travel, the more variations can occur which would lead to an incorrect positioning of the strips on the other material. Most importantly however, a stretch-and-separate process for the strips is disadvantageous to the goals of the applicant, namely to provide for a fast, reliable system for producing tampon laminates. If the weakening pre-cuts are not strong enough, the system of EP 1,035,819 does not allow for a very accurate separation of the strips, and in some cases could even cause unwanted tearing, variable edgings and variations in length of the strips. If the weakening pre-cuts are too strong, the strips might tear before reaching the actual acceleration roller which would cause the system to stop and have to be reset again. Even if the pre-cuts are applied to the desired effects, there will still be a variation in each strip due to local characteristics of the strip material, said variations are undesired. Also, the torn edges of the strips will not be as straight and controlled as desired.

There remains a need in the art, and even more so in the industry, for an improved continuous process for manufacturing multiple-layered sheets and tampon blanks, as well as apparatuses capable of performing these processes.

The present invention aims to resolve at least some of the problems mentioned above, by providing methods for a continuous process of intermittently joining strips of a first web material to a continuous second web material and apparatuses capable of performing these processes.

SUMMARY OF THE INVENTION

The present invention provides in a first aspect a method for manufacturing tampon laminate, comprising the following steps:
a. supplying a continuous first web material at a first speed, whereby said first speed is greater than zero, preferably whereby said first speed is constant;
b. cutting strips of the continuous first web material, whereby the strips are cut transversally, preferably perpendicularly, with respect to a longitudinal axis of the continuous first web material and preferably equidistantially repeated over the longitudinal axis of the continuous first web material;
c. supplying a continuous second web material at a second speed, which is higher than the first speed, preferably whereby said second speed is constant;
d. accelerating the strips from the first speed to the second speed;
e. bonding at least parts of the strips of the first web material to the continuous second web material, thereby forming a laminate structure;
characterized in the step of accelerating the strips from the first speed to the second speed is conducted essentially concurrently with the step of bonding at least parts of the strips of the first web material to the continuous second web material, thereby forming a laminate structure.

Obviously, the strips are conveyed or supplied at essentially the same first speed after step b, as the cutting preferably does not influence the speed of the first web material, be it continuous or in strips.

In a preferred embodiment, the step of accelerating the strips is conducted essentially concurrently with the step of cutting said one of the strips of the continuous web material.

In a preferred embodiment, the method comprises a step of applying predetermined breaking points on the continuous second web material, whereby the predetermined breaking points are applied transversally with respect to a longitudinal axis of the continuous second web material and preferably equidistantially repeated over the longitudinal axis of the continuous second web material, and whereby said step of applying predetermined breaking points is executed before bonding at least parts of the strips of the first web material to the continuous second web material.

In a further preferred embodiment, the method further comprises the steps of:
f. entirely separating the laminate structure along the predetermined breaking points, thereby creating laminate strips;
g. rolling the laminate strip so that the strip of the first web material forms an outer layer around the second web material of the laminate strip; and
h. optionally sealing the rolled laminate strip on the outer layer parallel to a longitudinal axis of the rolled laminate strip, thereby creating a closed tampon blank.

In a second aspect, the invention provides a method for intermittently providing strips of a continuous first web material onto a continuous second web material, comprising the following steps:
a. supplying the continuous first web material at a first speed, whereby said first speed is higher than zero and preferably is constant;
b. cutting strips of the continuous first web material, whereby the strips are cut transversally, preferably perpendicularly, with respect to a longitudinal axis of the continuous first web material;

c. supplying a continuous second web material at a different second speed, whereby the second speed is higher than the first speed, and preferably is constant;
d. accelerating the strips from the first speed to the second speed;
e. bonding at least parts of the strips to the continuous second web material;

whereby the step of accelerating one of the strips from the first speed to the second speed is conducted essentially concurrently with the step of bonding at least parts of said one of the strips to the continuous second web material and essentially concurrently with the step of cutting said one of the strips of the continuous web material.

It is worth noting that the cut strips of the first web material are further supplied at essentially the same first speed, as the step of cutting preferably does not influence the speed of the first web material, be it continuous or in strips.

In what follows, the referral to the preferred methods will apply to the method according to both the first as well as to the second aspect of the invention, unless expressly stated differently, or unless the statement cannot apply to one of the methods.

In a preferred embodiment of the methods according to both the first and the second aspect, the step of bonding at least parts of the strips comprises non-adhesive sealing, preferably heat-sealing, parts of the strips of the first web material to the continuous second web material.

In a preferred embodiment, the strips and the second web material have a substantially similar breadth when bonded to each other. More preferably, the breadths correspond approximately to the length of the finished tampon (blank).

In another preferred embodiment, the first web material has a substantially different breadth than the second web material.

In a preferred embodiment of the methods according to both the first and the second aspect, one of said web materials is a nonwoven web material, preferably a thermoplastic nonwoven web material, and another of said web materials is an absorbent fiber web material, preferably comprising rayon and/or cotton wool.

In a preferred embodiment of the methods according to both the first and the second aspect, the first web material is a non-adhesive material and not provided with adhesives. Optionally, the second web material is also a non-adhesive material and not provided with adhesives.

In a preferred embodiment of the methods according to both the first and the second aspect, the step of cutting strips of the continuous first web material is conducted upstream of the step of accelerating the strips from the first speed to the second speed over a distance along a longitudinal path of the first web material comprised between a length of a strip and 2 times the length of the strip, more preferably comprised between the length of the strip and 1.5 times the length of the strip, even more preferably comprised between the length of the strip and 1.2 times the length of the strip. Most preferably the step of cutting strips of the continuous first web material is conducted upstream of the step of accelerating the strips from the first speed to the second speed, over a distance along a longitudinal path of the first web material of about one time the length of the strip.

In a preferred embodiment of the methods according to both the first and the second aspect, the first speed and the second speed are essentially constant, and the step of supplying the strips of the first web material is conducted in a continuous manner.

In a preferred embodiment of the methods according to both the first and the second aspect, the step of accelerating the strips comprises gripping the strips and concurrently accelerating the strips to the second speed, whereby the second web material is used to grip the strips.

In a preferred embodiment of the methods according to both the first and the second aspect, the first speed and/or the second speed are adjustable.

A method according to the embodiments of the invention is particularly suitable as an intermediate process in the production of tampons and other sanitary products.

In a third aspect, the invention provides an apparatus for manufacturing a tampon laminate, comprising:
a. a sealing station, preferably comprising a sealing roller with one or more flexibly mounted sealing elements, and a counterpressure roller, for bonding strips of a first web material to a second web material;
b. a first conveying system comprising:
   i. one or more conveying means, preferably comprising one or more rollers, for conveying the first web material to the sealing station at a first speed;
   ii. a separation station, preferably comprising a cutting roller and a counterpressure roller, for cutting the strips of the first web material, preferably configured for cutting said strips equidistantly and transversally, more preferably perpendicularly, with respect to a conveying direction of the first web material;
c. a second conveying system comprising:
   i. one or more conveying means, preferably comprising one or more rollers, for conveying the second web material to the sealing station at an adjustable second speed, whereby the second speed is configured to be higher than the first speed;

characterized in that the sealing station comprises a set of two rolls, preferably the sealing roller and the counterpressure roller of the sealing station, arranged for pressing a strip to the second web material, thereby accelerating the strip to the second speed, said two rolls arranged to bond the strip to the second web material at least partially at essentially concurrently with accelerating said strip.

In a preferred embodiment of the apparatus, the second conveying system comprises a weakening station, said weakening station preferably comprising a weakening roller and a counterpressure roller, for applying predetermined breaking points on the second web material, whereby the predetermined breaking points are applied transversally with respect to a longitudinal axis of the continuous second web material and preferably equidistantially repeated over the longitudinal axis of the continuous second web material. Preferably the breaking points are applied linearly transversally. Said predetermined breaking points can be perforations, to later be torn off or separated fully and form separate sections of the second continuous web material. The predetermined breaking points can also be breaking lines or more general, areas of weakened tensile strength, where the second web material is partly cut and/or scraped off, and/or treated with heat and/or acid to create the desired breaking points.

In a preferred embodiment, the weakening station comprises a weakening roller and a counterpressure roller, whereby the sealing station comprises a sealing roller with one or more flexibly mounted sealing elements, and a counterpressure roller, and characterized in that the counterpressure roller of the sealing station is also the counterpressure roller of the weakening station.

In a preferred embodiment, the first conveying system comprises an extension, whereby the extension is adapted to collect the strips from the separation station and, preferably passively, guide the separated strips to the sealing station, and preferably whereby the first conveying system comprises a conveying roller for conveying the strips over the extension.

In a preferred embodiment, the bonding means comprises a sealing roller with one or more flexibly mounted sealing elements, and a counterpressure roller, and the sealing roller and the counterpressure roller of the bonding means are adapted to convey the second web material and accelerate the bonded strip of the first web material.

In a preferred embodiment, there is a pathway along the first web material between where strips are cut and where strips are bonded, whereby said pathway has a length about equal to a length of the strips.

In a preferred embodiment, the first conveying system comprises one or more, preferably two, air blowing means between the sealing station and the separation station, and the one or more air blowing means are adapted to guide the cut strips to the sealing station. Preferably, the air blowing means are adapted to hold the cut strips against the extension.

In a preferred embodiment, the first conveying system, and preferably the entire apparatus, is adapted to operate in a continuous manner.

In a fourth aspect, the invention comprises a method for calibrating an apparatus for performing a method according to the first and/or the second aspect, comprising the step of positioning the cutting station at a pathway distance from the sealing station, said pathway distance being essentially equal to the length of the strip to be laminated to the second web material, and the step of arranging the cutting interval of the cutting station such that a strip is cut from the first web material at essentially the moment at which the first web material has traveled a distance equal to the length of the strip to be laminated to the second web material.

DETAILED DESCRIPTION OF THE INVENTION

The present invention concerns a method for producing intermediate tampon products, such as tampon laminate, and an apparatus adapted for said method. As a result, the invention also concerns products of said method.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The term "nonwoven web material" means a sheet material having a structure of individual fibers or threads which are interlaid, but not in a regular manner such as occurs with knitting or weaving processes. Nonwoven fabrics or webs have been formed from many processes such as for example, meltblowing processes, spunbonding processes, and bonded carded web processes.

The term "thermoplastic" is meant to describe a material that softens when exposed to heat and which substantially returns to its original condition when cooled to room temperature.

The term "rayon" refers to a manufactured regenerated cellulose fiber, made from purified cellulose. It has a smooth, soft surface, and is therefore very suitable to be used in a tampon.

The term "concurrently" or "essentially concurrently" refers to the simultaneous or overlapping occurrence or execution of two or more events or steps.

The term "speed", both the first speed as the second speed, refers to the speed at which the first or second web material moves. This can for instance be the tangential speed at the surface of conveying rollers (and/or possibly the separation roller and/or the weakening roller).

The term "first web material" can also refer to already cut strips of the continuous web material. This is to be noted as the cutting of the strips occurs very fast and sudden. The first web material may be continuous at the start of a process, such as being conveyed (or a first section of the first web material being conveyed), but can be cut during the process. As such, the term "first web material" covers both the continuous first web material as the strips of the first web material.

The term "predetermined breaking points" refers to areas of weakened tensile strength, which are applied along a line, in this case usually in a line transversal with respect to the longitudinal axis of the web material. This creates "breaking lines", which allows the web material to be separated more easily into strips or sections, for instance by tearing or cutting, while still allowing the web material to be conveyed at high speeds without tearing at inopportune times. These predetermined breaking points can be applied by several different processes, for instance by applying perforations through small cuts, or by weakening certain zones by scraping off some of the material, thus weakening it. In other cases the weakened zones can be achieved by applying heat and/or acid to reduce the tensile strength. Note that combinations of the aforementioned methods are also possible, as well as others which have not been mentioned but are considered to be common knowledge in the field.

As mentioned, it is to be noted that the methods according to the first and second aspects have a lot of similarities, and will therefore in what follows be referred to as a single method, unless dealing with certain non-unitary aspects, at which point it will be indicated to which method the specification refers to.

The proposed methods of the invention no longer make use of discontinuous processes which, as argued and commonly accepted, are more taxing on the machinery, require more expensive machinery, provide less accurate results, operate at a lower total production speed and as a result of the first reason, cause more mechanical breakdowns and problems which are both expensive and time-consuming. The methods proposed by the applicant have the advantages of continuous methods used in other industries, such as higher speed of operation, cheaper machinery and/or maintenance, sturdiness, compactness, higher ease to fine-tune the process and others. The solution of using only continuous processes has however not easily been implemented in the field at hand and the few known methods all are flawed in one or more ways, yet the proposed method has succeeded in overcoming the flaws and other problems.

The length of a strip of the first web material differs from (in this case, smaller than) the length of the second web material the strip is associated with, and to which it will be (partly) applied. An example of this can be seen in FIG. 1A. This process necessitates different speeds at which the web materials are supplied. However, the difference in speed creates a problem when the separate materials are brought together. The different materials will be bonded once brought together, but in order to successfully perform the bonding, the speed of the strips must be changed. If the speed of the strips is not adjusted to match the speed of the second web material, the bonding could result into rips, tears or other impairments of at least one of the products, or into a poorly bonded result. The slower moving material (the strips) will be sped up to match the faster moving material (the second web material). By combining the execution of the step of bonding the strips to the second web material with the step of accelerating the strip, the machine or station for executing these steps can be combined into one single station, which saves on space and machinery.

The present invention provides in a first aspect a method for manufacturing a tampon laminate, comprising the following steps:
  a. supplying a continuous first web material at a first speed, whereby said first speed is greater than zero, preferably whereby said first speed is constant;
  b. cutting strips of the continuous first web material, whereby the strips are cut transversally, preferably perpendicularly, with respect to a longitudinal axis of the continuous first web material and preferably equidistantially repeated over the longitudinal axis of the continuous first web material;
  c. supplying a continuous second web material at a second speed, which is higher than the first speed, preferably whereby said second speed is constant;
  d. accelerating the strips from the first speed to the second speed;
  e. bonding at least parts of the strips of the first web material to the continuous second web material, thereby forming a laminate structure;
characterized in the step of accelerating the strips from the first speed to the second speed is conducted essentially concurrently with the step of bonding at least parts of the strips of the first web material to the continuous second web material, thereby forming a laminate structure.

Figure 2:
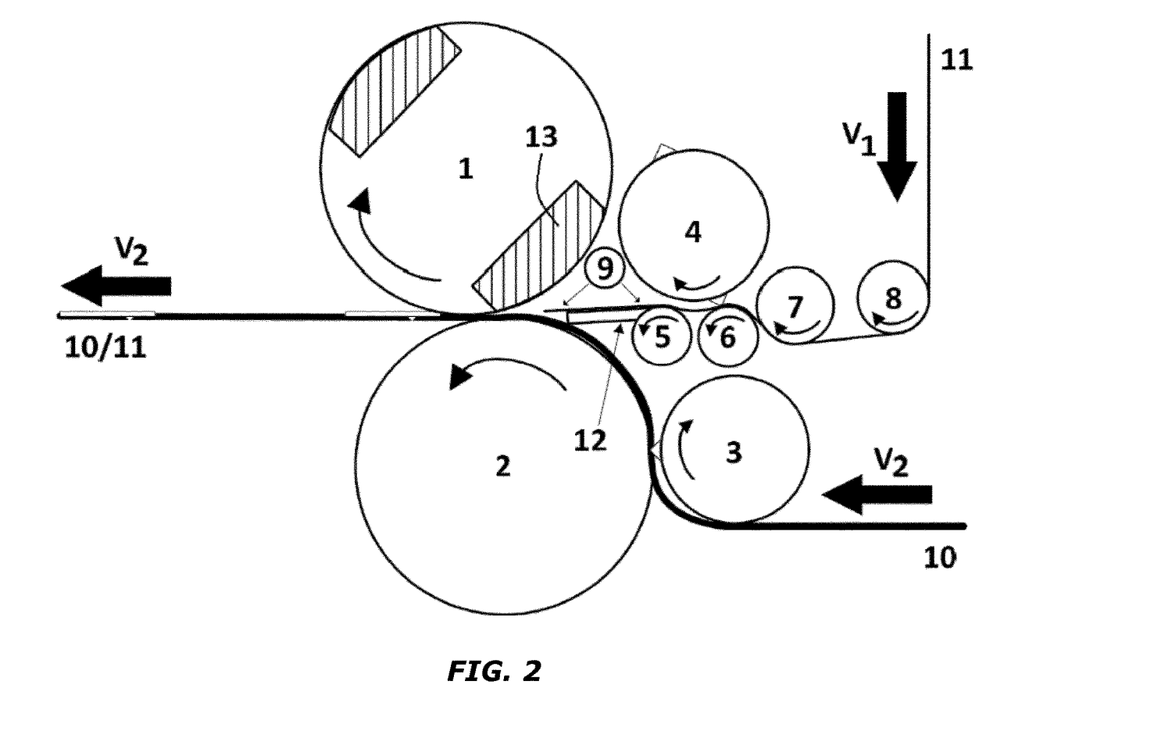
FIG. 2 shows a possible embodiment of the apparatus for manufacturing tampon blanks, according to the invention.

Simultaneous acceleration of the strips from the first speed to the second speed substantially concurrently with said bonding may be achieved by a roller arrangement as illustrated in FIG. 2 which allows for the strips of first web material to be pulled by a plurality of rollers (1, 2), forming a sealing station, and accelerate said first web from velocity v1 to velocity v2, generally by said pulling action, while at least a portion of said first web is being bonded to the continuous second web material by sealing means (or sealing elements 13) located on at least one of said plurality of rollers (1, 2), preferably a sealing roller (1) in rotational communication with a counter pressure roller (2) both rotating at a velocity v2.

In a preferred embodiment, cutting of the first web is carried out just prior to or substantially simultaneously with the acceleration step. This has the advantage of releasing a strip of the first web (typically traveling at velocity v1, and being pulled by the plurality of rollers 1, 2), as explained above) such that it is free to travel at a higher velocity v2 to limit undesirable stain and/or tears on the first web. Such may be advantageously achieved by locating one or more cutting means (or cutting elements) onto a surface of a separation roller (4) upstream said plurality of rollers (1, 2) forming the sealing station.

It is understood that the timing of the pulling, bonding and cutting described above may be readily adjusted to ensure the desired substantial simultaneous acceleration and bonding and/or cutting for different lengths of strips is achieved. Examples include and are not limited to: increasing or decreasing the pitch between sealing elements around the circumference of the sealing roller, increasing or decreasing the pitch between cutting elements around the circumference of the separation roller, increasing or decreasing the size of rollers, distance between cutting station and sealing station, and the like.

Although reference to the embodiment illustrated in FIG. 2 has been made for describing a suitable apparatus arrangement that would deliver the desired substantially simultaneous/concurrent acceleration step and bonding and/or cutting steps, it would be apparent to a person skilled in the art that alternative means of achieving this effect may be used.

Again, it is noted that the strips of the first web material are conveyed or supplied at essentially the same first speed as the first web material was.

In a preferred embodiment, the step of accelerating the strips is conducted essentially concurrently with the step of cutting said one of the strips of the continuous web material.

In a preferred embodiment, the method comprises a step of applying predetermined breaking points on the continuous second web material, whereby the predetermined breaking points are applied transversally with respect to a longitudinal axis of the continuous second web material and preferably equidistantially repeated over the longitudinal axis of the continuous second web material, and whereby said step of applying predetermined breaking points is executed before bonding at least parts of the strips of the first web material to the continuous second web material.

In a further preferred embodiment, the predetermined breaking points are linearly transversally applied on the continuous second web material, thereby creating breaking lines with reduced tensile strength. These breaking points can be perforations, cuts, zones weakened by treatment with heat or acid, or combinations. The created breaking lines allow for an easier separation of sections of the second web material.

In a further preferred embodiment, the method further comprises the steps of:

f. entirely separating the laminate structure along the predetermined breaking points, thereby creating laminate strips;

g. rolling the laminate strip so that the strip of the first web material forms an outer layer around the second web material of the laminate strip; and h. optionally sealing the rolled laminate strip on the outer layer parallel to a longitudinal axis of the rolled laminate strip, thereby creating a closed tampon blank.

In a second aspect, the invention provides a method for intermittently providing strips of a continuous first web material onto a continuous second web material, comprising the following steps:

a. supplying the continuous first web material at a first speed, whereby said first speed is higher than zero and preferably is constant;

b. cutting strips of the continuous first web material, whereby the strips are cut transversally, preferably perpendicularly, with respect to a longitudinal axis of the continuous first web material;

c. supplying a continuous second web material at a different second speed, whereby the second speed is higher than the first speed, and preferably is constant;

d. accelerating the strips from the first speed to the second speed;

e. bonding at least parts of the strips to the continuous second web material;

characterized in that the step of accelerating one of the strips from the first speed to the second speed is conducted essentially concurrently with the step of bonding at least parts of said one of the strips to the continuous second web material and essentially concurrently with the step of cutting said one of the strips of the continuous web material.

Again, it is obvious that the strips continue to move at essentially the same first speed.

In another preferred embodiment, the first web material has a substantially different breadth than the second web material, as this could allow the production of laminate structures (or subsequent products such as tampon blanks) with an overhanging section of the first web material or the second web material on one or both transversal ends of the laminate structure. For instance, should the first web material have a greater breadth than the second web material, this could be used to form a tampon blank where the thusly created overhanging section on one end of the tampon blank (or both ends) could be used to (partly) close the end (or ends) of the tampon blank. Alternatively, should the first web material have a smaller breadth than the second web material, this could be used to form a tampon blank with a smaller covering layer of the first web material.

In a preferred embodiment of the methods according to both the first and the second aspect, the step of bonding at least parts of the strips comprises non-adhesive sealing, preferably heat-sealing, the parts of the strips of the first web material to the continuous second web material. Alternatively the step of bonding at least parts of the strips can comprise other bonding steps, for instance more specific forms of heat-sealing, such as ultrasonic welding, hot meld adhesive, induction welding (with modifications to the materials) and others. All of these processes allow fast bonding of the two materials, without requiring elaborate machinery.

In a preferred embodiment of the methods according to both the first and the second aspect, one of said web materials is a nonwoven web material, preferably a thermoplastic nonwoven web material, more preferably a bicomponent polyethylene/polypropylene material or a bicomponent polyethylene/polyester, for instance with an area density of about 12 g/m$^2$. Another of said web materials is an absorbent fiber web material, preferably comprising rayon and/or cotton wool. Preferably the first web material is the absorbent fiber web material, and the second web material is the nonwoven web material, more preferably the thermoplastic nonwoven web material. The choice for a thermoplastic nonwoven web material allows heat-sealing and other bonding processes to be used. The use of an absorbent fiber web material is advantageous as the purpose of the product of the method is to create an absorbent item.

In a preferred embodiment of the methods according to both the first and the second aspect, the first web material is a non-adhesive material and not provided with adhesives. Optionally, the second web material is also a non-adhesive material and not provided with adhesives.

In a preferred embodiment of the methods according to both the first and the second aspect, the step of cutting strips of the continuous first web material is conducted upstream of the step of accelerating the strips from the first speed to the second speed over a distance along a longitudinal path of the first web material comprised between a length of a strip and 2 times the length of the strip, more preferably comprised between the length of the strip and 1.5 times the length of the strip, even more preferably comprised between the length of the strip and 1.2 times the length of the strip. Most preferably the step of cutting strips of the continuous first web material is conducted upstream of the step of accelerating the strips from the first speed to the second speed, over a distance along a longitudinal path of the first web material of about one time the length of the strip. By reducing the distance between where the strips are cut and where the strips are subsequently accelerated to a length comparable to the length of the strip, the strips will only need to traverse a short path once separated, before they are accelerated and bonded. As long as the strips are not cut, they are conveyed or supplied at the first speed towards where they are bonded. However, once cut, it is the purpose of the method to execute the step of accelerating and bonding the strips as soon as possible after cutting the strip, preferably at completion of the cutting of the strip.

In a further preferred embodiment of the methods described herein, the maximum length A between the longitudinal ends of two consecutive strips of first web material that have been bonded with the second web material can be determined according to Formula 1:

$$A = (v2 - v1) * B / v1 \qquad \text{Formula 1}$$

Wherein, v1 is the speed of the first web material, v2 is the speed of the second web material, B is the distance between where said strips are cut and where the strips are subsequently accelerated.

In a preferred embodiment of the methods according to both the first and the second aspect, the first speed and the second speed are essentially constant and non-zero, and the step of supplying the strips of the first web material is conducted in a continuous manner.

In a preferred embodiment of the methods according to both the first and the second aspect, the step of accelerating the strips comprises gripping the strips and concurrently accelerating the strips to the second speed, whereby the second web material is used to grip the strips.

In a further preferred embodiment of the methods according to both the first and the second aspect, the second web material is supplied from below the strips and/or the first web material. This enables the strips to fall upon the second web material and through the friction between the two web materials, be pulled further towards the sealing station.

In a further preferred embodiment of the methods, the step of accelerating the strips comprises gripping the strips and concurrently accelerating the strips to the second speed, whereby the second web material is used to grip the strips. By using the second web material to grip the strips, and thereby accelerating the strips to the second speed, there is no need for a separate station to accelerate the strips, and thereafter supply the accelerated strips to the second web material. This allows for a more efficient process.

In a further preferred embodiment of the methods, the first speed and the second speed are essentially constant, whereby the step of supplying the strips of the first web material is conducted in a continuous manner. The advantages of a continuous process over a discontinuous one have been stated before and are otherwise well known. It is to be noted that the first speed and the second speed can preferably be adjusted in order to satisfy certain design conditions for the desired article, for example the length of the strips, between the predetermined breaking points on the second web material, and/or ratio between the strip and the length of the second web material associated with the strip.

In a further preferred embodiment of the methods, the step of accelerating the strips to the second speed, and the step of bonding the strips to the second web material is executed not only concurrently, but also in essentially one location. A method according to the embodiments of the invention is particularly suitable as an intermediate process in the production of tampons and other sanitary products.

In a third aspect, the invention provides an apparatus for manufacturing tampon laminate, comprising:
a. a sealing station, preferably comprising a sealing roller with one or more flexibly mounted sealing elements, and a counterpressure roller, for bonding strips of a first web material to a second web material;
b. a first conveying system comprising:
  i. one or more conveying means, preferably comprising one or more rollers, for conveying the first web material to the sealing station at a first speed;
  ii. a separation station, preferably comprising a cutting roller and a counterpressure roller, for cutting the strips of the first web material, preferably configured for cutting said strips equidistantly and transversally, more preferably perpendicularly, with respect to a conveying direction of the first web material;
c. a second conveying system comprising:
  i. one or more conveying means, preferably comprising one or more rollers, for conveying the second web material to the sealing station at a second speed, whereby the second speed is configured to be higher than the first speed;
characterized in that the sealing station comprises an accelerating means and a bonding means, and is adapted to accelerate a strip from the first speed to the second speed with the accelerating means, and concurrently bond at least parts of the strip of the first web material non-adhesively to the second web material with the bonding means, thereby forming a laminate structure, preferably whereby the bonding means comprises or is the accelerating means.

More preferably, the apparatus of above is characterized in that the sealing station comprises a set of two rolls, preferably the sealing roller and the counterpressure roller of the sealing station, arranged for pressing a strip to the second web material, thereby accelerating the strip to the second speed, said two rolls arranged to bond the strip to the second web material at least partially at essentially concurrently with accelerating said strip.

In a preferred embodiment, the first speed and/or the second speed is adjustable.

In a further preferred embodiment, the bonding means comprises one or more heat-sealing means, adapted to heat-seal the strips to the second web material. The heat-sealing means can be one or more flexibly mounted sealing elements on a sealing roller, which is thusly adapted to intermittently heat-seal the strips to the second web material.

In a further preferred embodiment, the second conveying system comprises a weakening station, said weakening station preferably comprising a weakening roller and a counterpressure roller, for applying predetermined breaking points on the second web material, whereby the predetermined breaking points are applied transversally with respect to a longitudinal axis of the continuous second web material, thereby creating breaking lines, and preferably equidistantially repeated over the longitudinal axis of the continuous second web material.

In a more preferred embodiment, the weakening station is a perforation station, and comprises a perforation roller as the weakening roller. The predetermined breaking points are perforations and are applied linearly transversally to the longitudinal axis of the second web material, thereby creating breaking lines which allow for an easier separation of sections of the second web material, by fully separating the breaking lines.

In a possible embodiment, the weakening station comprises a weakening roller and a counterpressure roller, whereby the sealing station comprises a sealing roller with one or more flexibly mounted sealing elements, and a counterpressure roller, and characterized in that the counterpressure roller of the sealing station is also the counterpressure roller of the weakening station. Again, this reduces space requirements and ensures a constant speed of these two stations, as the counterpressure rollers will generally support the web material that is conveyed. Furthermore, there is less danger of the second web material incurring disturbances as the second web material would be transported by a single counterpressure roller, instead of having to be transferred from a first counterpressure roller to a second one. This could cause the web material to curl up and cause jams in the apparatus, which are averted by using a single counterpressure roller for both applying predetermined breaking points (or weakening the second web material) and bonding/accelerating. Furthermore, by using flexibly mounted sealing elements, it is no longer necessary for the counterpressure roller to compensate changes in the thickness of the second web material, as the sealing elements will compensate for this. This allows the counterpressure roller to act as a purely passive element in the apparatus, which is both cheaper and sturdier. Other benefits are that the sealing elements are much smaller and lighter than the counterpressure roller, and therefore will adjust to the deviations much faster, due to the much lower inertia of the sealing elements. This will allow to compensate for small and/or fast variations, for which prior art apparatuses might not be able to compensate due to the high inertia. The lowered inertia also reduces or avoids kick-back errors, resulting from recoil after compensations. A possible embodiment for the flexibly mounted sealing elements are sealing elements which are mounted on the sealing roller with flexible springs.

In a further preferred embodiment, the first conveying system comprises an extension, whereby the extension is adapted to collect the strips from the separation station, preferably before they are separated, and guide the separated strips to the sealing station, and preferably whereby the first conveying system comprises a conveying roller for conveying the strips over the extension. This extension can take the shape of a ramp, which interacts with the separation station in order to collect the strips when cut or separated, and is adapted to offer the strips to the sealing station. Preferably, the extension operates passively. The extension does not pull or push the strips, but only guides the strips which are pushed or pulled by other means, comprised in the first conveying means, such as conveying rollers.

In a possible embodiment, the separation station comprises a cutting roller and a counterpressure roller. The first web material is conveying so that it runs between the cutting roller and the counterpressure roller, and is supported by the counterpressure roller, thus being cut into the desired strips by the cutting roller. The cut strips are also supported by the counterpressure roller. The extension (or other conveying means) and the counterpressure roller are adapted so that the extension (or the other conveying means) collects the strips from the counterpressure roller. As the strip still will be pushed forward at least until the strip is cut, the strip will be conveyed further along the extension (or the other conveying means), towards the sealing station. Preferably, once the strip has been cut, the strip will still be pushed forward by the counterpressure roller, along the extension (or the other conveying means) towards the sealing station. Once the strip reaches the sealing station, it will be accelerated by the sealing station and bonded to the second web material.

In a further preferred possible embodiment, the counterpressure roller has at least one and preferably a number of annular grooves on the surface. The extension has saw teeth, corresponding with the pattern of the annular grooves on the surface, and is mounted so that part of the saw teeth extend into the annular grooves. This allows a smooth collecting of the strips by the extension, and ensures that no strips can pass between the extension and the counterpressure roller, which would disturb the process and could potentially cause mechanical problems. In this preferred embodiment, the extension itself is a passive element, in that it simply guides the movement of the strips/first web material, and does not impose a speed on the strip/first web material.

It is alternatively possible for the extension to be an active element that pulls or pushes the strips/first web material further towards the sealing station at the first speed. Furthermore, it is possible that the extension comprises an active accelerating element adapted to accelerate the strip once it is cut. To make sure the strip is only accelerated when cut, it is necessary to place such an active accelerating element far enough from where in the separation station the cut is made.

Alternatively, the counterpressure roller of the separation station conveys the first web material to a conveying roller, which conveys the first web material at the same (tangential) speed as it is supplied to the separation station. The extension and the conveying roller are adapted so that the extension collects the strips from the conveying roller. As the strip still will be pushed forward at least until the strip is cut, the strip will be conveyed further along the extension, towards the sealing station. Preferably, once the strip has been cut, the strip will still be pushed forward by the conveying roller, along the extension towards the sealing station. Once the strip reaches the sealing station, it will be accelerated by the sealing station and bonded to the second web material. In a further preferred possible embodiment, the conveying roller has at least one and preferably a number of annular grooves on the surface. The extension has saw teeth, corresponding with the pattern of the annular grooves on the surface, and is mounted so that part of the saw teeth extend into the annular grooves of the conveying roller. The advantages of this configuration have been mentioned above, where optional modifications have been mentioned as well.

In a further preferred embodiment, the bonding means comprises a sealing roller with one or more flexibly mounted sealing elements, and a counterpressure roller, and the sealing roller and the counterpressure roller of the bonding means are adapted to guide and/or convey the second web material and accelerate the bonded strip of the first web material. By having the counterpressure roller of the sealing station also function as a guide and/or conveyor for the second web material and accelerate the strips of the first web material, space is saved and no unnecessary elements are used in the apparatus. Unnecessary elements generally create a more complicated process and can cause problems in attuning the separate elements to cooperate harmoniously, for instance matching speeds, frequencies and so on.

In a further preferred embodiment, there is a pathway along the first web material between where strips are cut and where strips are bonded, whereby said pathway has a length comprised between a length of a strip and 2 times the length of the strip, preferably comprised between the length of the strip and 1.5 times the length of the strip, more preferably comprised between the length of the strip and 1.2 times the length of the strip. Most preferably, said pathway has a length about equal to a length of the strips. As mentioned, the separated strip will need to be supplied to the sealing station, preferably over a minimal distance. The minimal distance would be the length of a single strip, therefore the distance between the aforementioned stations should approximate this length as much as possible, thus allowing a process in which the strip is cut and essentially concurrently accelerated, and preferably also bonded to the second web material.

In a further preferred embodiment, the maximum length A between the longitudinal ends of two consecutive strips of first web material that have been bonded with the second web material can be determined according to Formula 1 above. In a further preferred embodiment, the first conveying system comprises one or more, preferably two, air blowing means between the sealing station and the separation station, and the one or more air blowing means are adapted to guide the cut strips to the sealing station. Preferably, the air blowing means are adapted to hold the cut strips against the extension. The air blowing means provide constant air streams on the first web material, to make sure it pressed against the extension and cannot curl up and possibly miss the sealing station. Alternatively (or additionally) one or more suction means can be comprised in the conveying system, in order to ensure that the strips are efficiently and securely supplied to the sealing station.

In a further preferred embodiment, one of said web materials is a nonwoven web material, preferably a thermoplastic nonwoven web material, and another of said web materials is an absorbent fiber web material, preferably comprising rayon and/or cotton wool. Preferably the first web material is the absorbent fiber web material, and the second web material is the nonwoven web material, more preferably the thermoplastic nonwoven web material. The choice for a thermoplastic nonwoven web material allows heat-sealing and other bonding processes to be used. The use of an absorbent fiber web material is advantageous as the purpose of the product of the method is to create an absorbent item.

In a further preferred embodiment, the step of accelerating one of the strips starts essentially at completion of the step of cutting said one of the strips. It is the intention of the invention to allow only the shortest possible time between these steps, as this firstly implies a method that can be compactly executed, and secondly reduces the risk of disturbances on the strips in between the step of cutting and the step of accelerating (and the bonding).

In a further preferred embodiment, the first conveying system, and preferably the entire apparatus, is adapted to operate in a continuous manner.

It is furthermore to be noted that, both for methods and for apparatus, it is possible to change the length of the strips, of the distance between the predetermined breaking points and/or the ratio of both. This can be achieved for instance by adjusting first and/or the second speed, by adjusting the separation and/or weakening station, such as replacing the separation roller and/or the weakening roller (more blades and/or larger diameter) and/or changing the rotational speeds of the separation and/or the weakening roller. Please note that the separation roller and/or the weakening roller do not necessarily actively convey the web materials (more appropriate would be "guiding the web materials"), and are thus not required to have a tangential speed at their edge that is equal to the conveying speed of the web material that is manipulated by the roller in question. However, this is preferably the case as this would synchronize the process flow and would reduce possible recoil effects due to a mismatch in operation speeds. Furthermore, when changing the length of the strips it is recommended to reposition the separation station with respect to the sealing station (or vice versa), as there is preferably a distance along the first web material between the sealing station and the separation station of about a length of one of the strips. If the length of the strip is to be increased or reduced, the sealing station and the separation station are to be put further apart or closer together. Therefore, the apparatus is preferably adapted to that the separation roller can be easily replaced.

Furthermore, the apparatus is preferably adapted to that the weakening roller can be easily replaced. Also, the apparatus is preferably adapted so that the distance between the separation roller (or separation station) and the sealing station can be easily adjusted. In a fourth aspect, the invention provides a method for calibrating an apparatus for performing a method according to the first and/or the second aspect, comprising the step of positioning the cutting station at a pathway distance from the sealing station, said pathway distance being essentially equal to the length of the strip to be laminated to the second web material, and the step of arranging the cutting interval of the cutting station such that a strip is cut from the first web material at essentially the moment at which the first web material has traveled a distance equal to the length of the strip to be laminated to the second web material.

Figure 3:
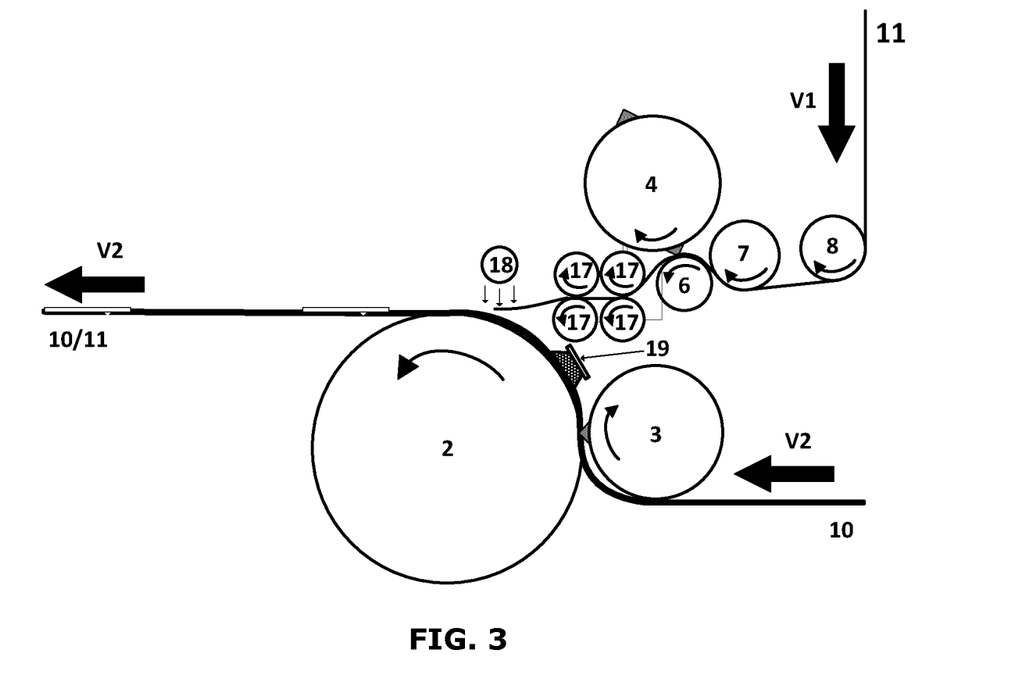
FIG. 3 shows an alternative embodiment of the apparatus for manufacturing tampon blank, according to the invention.

For example, in an alternative embodiment, simultaneous acceleration of the strips from the first speed to the second speed substantially concurrently with said bonding may be achieved by a roller arrangement (such as illustrated in FIG. 3) which allows the strips of first web material being pulled by a quantity of one or more rollers (17), forming an acceleration station typically operating at changeable velocities, and an air blowing means (18), forming a bonding station, and a glue coating means (19), forming a coating station upstream of said bonding station, preferably wherein each of said quantity of one or more rollers rotate at a velocity v2 to accelerate the strips from a velocity v1 to said velocity v2. More preferably, said acceleration occurs substantially concurrently with a cut being performed on the first continuous web material. An advantage being that the acceleration of the strip of first web material from velocity v1 to velocity v2 occurs while at least a portion of said strip of first web material is pressed on the continuous second web material by said air blowing means at said bonding station, preferably wherein said continuous second web has been, typically predeterminedly, at least partly coated with an adhesive by said glue coating means at said coating station upstream of said bonding station. The invention is further described by the following non-limiting examples which further illustrate the invention, and are not intended to, nor should they be interpreted to, limit the scope of the invention.

The present invention will be now described in more details, referring to examples that are not limitative.

EXAMPLES

Example 1: Tampon Blank

Figure 1A:
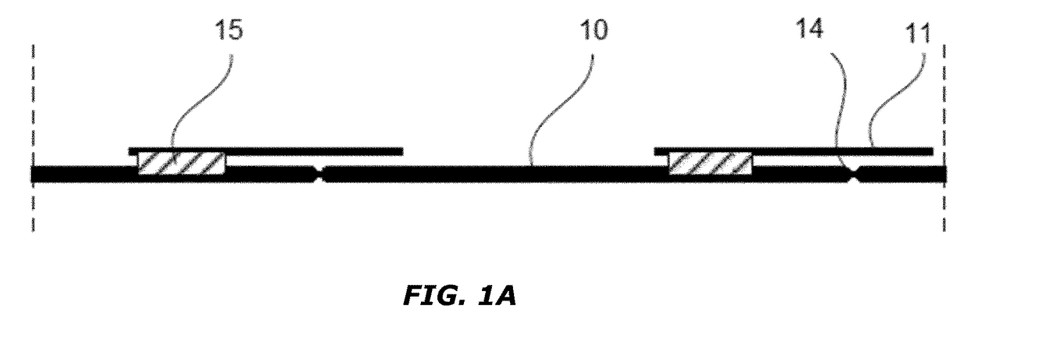
FIG. 1A shows a laminate, comprising intermittently placed strips of a first web material bonded to a perforated second web material.

In FIG. 1A, the product of the methods disclosed in this document are shown, wherein a continuous second web material (10) is provided with predetermined breaking points, preferably along a line transversal to its longitudinal axis, equidistantially along its longitudinal axis, and is intermittently provided with strips of a first web material (11), of a different length than between subsequent predetermined breaking points (14). In this case, the strips (11) are shorter than the distance between the subsequent predetermined breaking points (14) of the second web material (10). The strips (11) are then partly bonded to an end of the second web material (10), preferably so that a part of the strip (11) extends beyond said end of the second web material (10). The bonding of at least parts of the strip (11) to the second web material (10) can be done in a plurality of manners, one of which being heat-sealing through application of heat, or alternatively ultrasonic welding. Possible dimension for the web materials are a length of 250 mm between subsequent predetermined breaking points, and a length of 125 mm for the strip (11). The part of the strip that is bonded (15) to the second web material (10) can for instance extended over a distance of 40 mm.

Figure 1B:
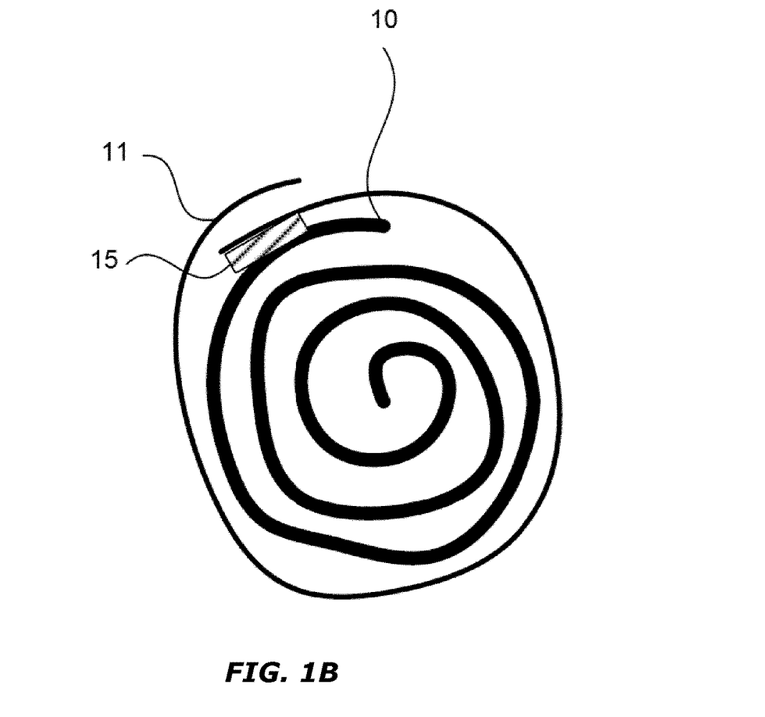
FIG. 1B shows a rolled tampon blank.
Figure 1C:
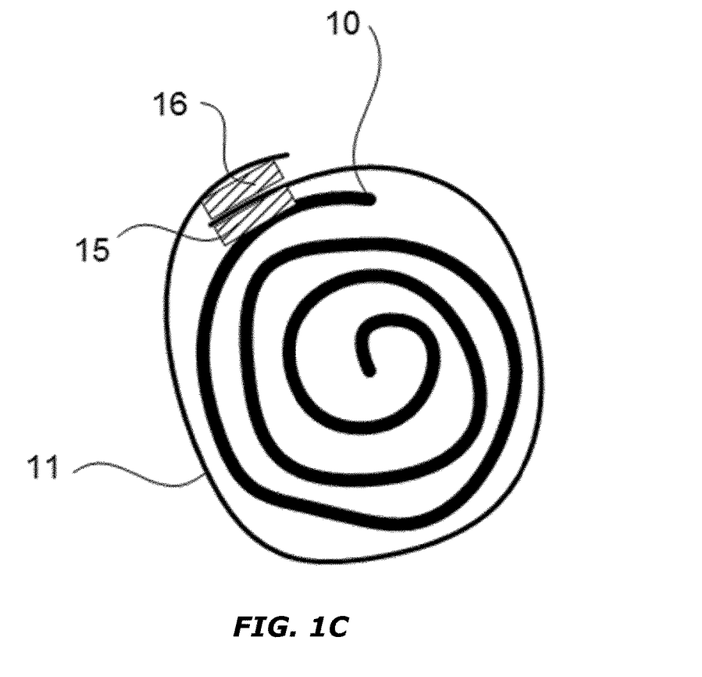
FIG. 1C shows a closed, rolled tampon blank.

It is important for the production process that the second web material (10) is provided with predetermined breaking points (14), but not entirely separated, or too strongly weakened, in order for said second web material (10) to be pulled through the apparatus as a continuous stream. After the strips (11) are bonded, it is possible to fully separate the second web material (10) at the predetermined breaking points (14), thus creating identical laminated strips, comprising both the first (11) and the second web material (10). These can subsequently be rolled in a matter according to FIG. 1B, with the second web material (10) on the interior of the tampon blank, and the first web material (11), the original strip, as an outer layer. After the tampon blank has been rolled, a second sealing operation can be executed to close the outer layer of the first web material, the original strip, around the tampon blank with a seal (16), as can be seen in FIG. 1C.

By carefully choosing the outer layer of first web material (11) and the first web material (11) itself, many advantageous effects are achieved, for instance it increases the stability of the tampon, thus reducing deformations and generating a more aesthetically pleasing appearance, which is instrumental in appealing to a customer and providing the assurance of quality of a hygienic and very intimate product.

Furthermore, the application of the tampon is easier as the outer layer of the first web material (11) is smoother than the interior second web material (10). This way, application of the tampon is made easier, while still allowing for optimal absorbance of menses and other fluids. Also, by having a stronger, smoother outer layer of first web material (11), the interior second web material (10) is not exposed to the forces and frictions of the machinery it is run through and fibers of the interior material cannot detach themselves. If too many fibers would detach during the production process, not only would this cause deterioration in the produced tampons, but this could also clog up the machinery that produces the tampons. Lastly and most importantly, it is of the highest importance for the tampon that as few as possible absorbent fibers can detach themselves during use, as these could otherwise accumulate in the body of the consumer. By having a stronger, outer layer of first web material (11) as can be seen in FIG. 1C, the fibers of the interior second web material (10) will not detach as easily as they are less exposed to forces or frictions, and even should they detach themselves, will likely be contained within the outer layer of first web material (11).

In a possible embodiment, the first web material is a soft carded thermobonded nonwoven material with a smooth surface. The smooth surface, as mentioned, aids in the application of the hygienic product. The first web material is preferably hydrophilic, and can for instance be a 100% mix of polyethylene (PE) and polyester, preferably polyethylene terephthalate (PET). Further characteristics of the proposed embodiment is an area density of about 12 g/m$^2$ (according to WSP 130.1), a tensile strength at maximal force in the machine direction (lengthwise) of about 16 N/5 cm, a tensile strength at maximal force in the cross machine direction (breadthwise) of about 2 N/5 cm, an elongation at maximal force in the machine direction of about 25%, an elongation at maximal force in the cross machine direction of about 30% (all according to WSP 110.4) and a liquid strike-through time (according to WSP 70.3) of about 2.5 s. These characteristics have been measured by WSP protocols.

Example 2: Improved Apparatus

In FIG. 2, a possible configuration is shown of an apparatus for manufacturing tampon blanks. However, it is to be noted that not all of these elements are strictly necessary and/or could be replaced by other elements with similar functions in order to accomplish the objective of the invention, and that the invention is therefore not limited to this embodiment.

In the apparatus, a first continuous web material (11) is provided continuously at a first speed ($v_1$) to a first conveying system (7, 8, 5). Note that the elements of the first conveying system (7, 8, 5) can also be logically grouped under a different station or system, however this does not affect the function. In this embodiment, the first conveying system (7, 8, 5) comprises a pulling roller (7) for pulling/unwinding the first web material (11) from a web roll or other sources, and conveying it further along. The first conveying system (7, 8, 5) further comprises a guiding roller (8) for correctly feeding the first web material (11) to further stations. The guiding roller (8) possibly comprises a guiding notch for centering the first web material (11) in case of deviations of the path of the first web material (11) while being pulled from the web roll or other sources. Subsequently, the first web material (11) is conveyed through the separation station (4, 6), where a separation roller (4) cuts the first web material (11) into strips in concert with a counterpressure roller (6) which conveys the first web material (11) and the cut strips and provides a base on which the first web material (11) can be cut by the separation roller (4). The separation roller (4) in this example comprises two blades placed at opposite sides of the separation roller (4), however other versions can be used, having 1, 3, 4, 5, 6, 8, 10 or more blades. Preferably, the separation roller (4) and the counterpressure roller (6) rotate at equal (or at least similar) tangential surface speeds in order to provide a clean cut without dragging the first web material. In order to change the length of the strips cut by the separation roller (4), a separation roller (4) with a different diameter and/or a different amount of blades and/or a different rotational speed can be used. When the first web material (11) has passed the separation station (4, 6), not necessarily as a cut strip yet, the first web material (11) is conveyed further by a conveying roller (5) of the first conveying system (7, 8, 5). The conveying roller (5) of the first conveying system (7, 8, 5) is adapted to push the first web material (11) further along to a sealing station (1, 2). An extension (12) is present in the form of a ramp which collects the first web material (11) from the conveying roller (5). This is for instance efficiently done as mentioned before, by the conveying roller (5) having a grooved surface, and the extension (12) having matching teeth which can be received in the grooves of the surface of the conveying roller (5). Furthermore, air blowing means (9) are present which provide constant air streams to press the first web material (11) against the extension (12), thus reducing the risk of the first web material (11) curling up. The conveying roller (5) pushes the first web material (11) further along the extension (12) until the separation roller (4) cuts a strip of the first web material (11), at which point the strip is offered to the sealing station (1, 2).

A second web material (10) is provided continuously at a second speed ($v_2$) to a weakening station (3, 2), comprising a weakening roller (3) and a counterpressure roller (2). The weakening roller in this case is a perforation roller (3) and comprises one or more (2, 3, 4, 5, 6, 8, 10 or more) blades that apply a perforation line on the second web material (10). As mentioned, the weakening station can also scrape off material in zones of the second web material, or treat the second web material with acid or heat to create the predetermined breaking points, or even employ a combination of more than one of said methods. In the preferred embodiment, the weakening station is a perforation station and the perforation roller comprises blades to form a zigzag pattern along the perforation line. The distance between subsequent perforation lines can be adapted by using a different perforation roller (3) with a different number of blades and/or a different diameter and/or different rotational speeds. Note however that the perforation station (2, 3), or parts thereof, also acts as a conveying system for the second web material (10). After being perforated, the second web material (10) is conveyed over the counterpressure roller (2) of the perforation station (2, 3) to the sealing station (1, 2). The counterpressure roller (2) of the perforation station (2, 3) is also the counterpressure roller (2) of the sealing station (1, 2).

The strips of the first web material (11) are supplied to the sealing station and joined with the second web material (10). At this point, the strips are cut in the separation station (4, 6), and concurrently accelerated by entering the sealing station (1, 2), where they are bonded to the second web material (10). In this embodiment, the sealing station comprises a sealing roller (1) and the counterpressure roller (2). The sealing roller (1) comprises one or more, preferably 2, but alternatively 3, 4, 5, 6, 8, 10 sealing elements (13). These sealing elements (13) are flexibly mounted, for instance with flexible springs in order to compensate for small deviations in thickness of the first or second web material (11, 10). The sealing elements (13) can for instance be heating elements designed to heat-seal at least parts of the strips of the first web material (11) to the second web material (10).

Preferably, rollers for the first web material and/or strips (7, 8, 4, 6 and 5) rotate at an equal tangential speed at their surface, namely the first speed ($v_1$). Rollers for the second web material, and the rollers of the second web material rotate at an equal tangential speed at their surface, namely the second speed ($v_2$). The tangential speeds comes down to the speed at which the web material is being conveyed over the rollers at hand. Optionally, the separation roller (4) can rotate at different tangential surface speeds than the first speed, as it does not actually carry the first web material (11). Furthermore, with adaptations so that the weakening roller (3) does not carry the second web material (10), the weakening roller (3) can also rotate at a different tangential surface speed than the second speed. However, it is preferred that they do.

Example 3: Further Improved Apparatus

As a further improvement to the apparatus described in Example 2, the extension (12) and blowing means (9) are replaced with a conveyor belt assembly comprising at least one belt and one or more belt driving means, wherein said belt is arranged to travel at a speed v1.

It is supposed that the present invention is not restricted to any form of realization described previously and that some modifications can be added to the presented example of fabrication without reappraisal of the appended claims. For example, the present invention has been described referring to tampons, but it is clear that the invention can be applied to other hygienic products or even more generally other products requiring lamination of two different web materials.

The invention claimed is:

1. Method for manufacturing tampon laminate, comprising the steps of:
   a. supplying a continuous first web material at a first speed, whereby said first speed is greater than zero;
   b. cutting strips of the continuous first web material, whereby the strips are cut transversally with respect to a longitudinal axis of the continuous first web material and equidistantially repeated over the longitudinal axis of the continuous first web material;
   c. supplying a continuous second web material at a second speed, which is higher than the first speed;
   d. accelerating the strips from the first speed to the second speed;
   e. bonding at least parts of the strips of the first web material to the continuous second web material, thereby forming a laminate structure;
   characterized in that the step of accelerating the strips from the first speed to the second speed is conducted essentially concurrently with the step of bonding at least parts of the strips of the first web material to the continuous second web material, thereby forming a laminate structure, and in that the step of accelerating the strips is conducted essentially concurrently with the step of cutting strips of the continuous web material.

2. Method according to claim 1, characterized in that the step of bonding at least parts of the strips, comprises non-adhesive sealing parts of the strips of the first web material to the continuous second web material.

3. Method according to claim 2, whereby the non-adhesive sealing is heat-sealing.

4. Method according to claim 1, whereby one of said first and second web materials is a nonwoven web material and the other is an absorbent fiber web material.

5. Method according to claim 4, whereby one of said first and second web materials is a thermoplastic nonwoven web material, and the other is an absorbent fiber web material comprising rayon and/or cotton wool.

6. Method according to claim 1, comprising a step of applying predetermined breaking points on the continuous second web material, whereby the predetermined breaking points are applied transversally with respect to a longitudinal axis of the continuous second web material and equidistantially repeated over the longitudinal axis of the continuous second web material, and whereby said step of applying predetermined breaking points is executed before bonding at least parts of the strips of the first web material to the continuous second web material.

7. Method according to claim 6, comprising the steps of:
   f. entirely separating along the predetermined breaking points of the laminate structure, thereby creating laminate strips;
   g. rolling the laminate strip so that the strip of the first web material forms an outer layer around the second web material of the laminate strip; and
   h. optionally sealing the rolled laminate strip on the outer layer parallel to a longitudinal axis of the rolled laminate strip, thereby creating a tampon blank.

8. Method according to claim 1, whereby said first speed is constant, the strips are cut perpendicularly with respect to the longitudinal axis, and said second speed is constant.

9. Method for intermittently providing strips of a continuous first web material onto a continuous second web material, comprising the following steps:
   a. supplying the continuous first web material at a first speed, whereby said first speed is higher than zero;
   b. cutting strips of the continuous first web material, whereby the strips are cut transversally with respect to a longitudinal axis of the continuous first web material;
   c. supplying a continuous second web material at a different second speed, whereby the second speed is higher than the first speed;
   d. accelerating the strips from the first speed to the second speed;
   e. bonding at least parts of the strips to the continuous second web material;
   characterized in that the step of accelerating one of the strips from the first speed to the second speed is conducted essentially concurrently with the step of bonding at least parts of said one of the strips to the continuous second web material and essentially concurrently with the step of cutting said one of the strips of the continuous web material.

10. Method according to claim 9, whereby said first speed is constant, the strips are cut perpendicularly with respect to the longitudinal axis, and the second speed is constant.

* * * * *